United States Patent
Gilman et al.

[11] Patent Number: 5,891,077
[45] Date of Patent: Apr. 6, 1999

[54] THIN FILM WOUND DRESSING WITH REMOVABLE FORAMINOUS BACKING LAYER

[75] Inventors: Thomas H. Gilman, Spring Grove; Eric D. Ellingson, Mount Prospect, both of Ill.

[73] Assignee: Hollister Incorporated, Libertyville, Ill.

[21] Appl. No.: 955,512

[22] Filed: Oct. 21, 1997

Related U.S. Application Data

[63] Continuation-in-part of Ser. No. 818,504, Mar. 14, 1997.

[51] Int. Cl.⁶ ..................................................... A61F 13/00
[52] U.S. Cl. ................................ 602/57; 602/44; 602/52; 602/54; 602/55; 602/59
[58] Field of Search ....................... 602/41–59; 128/888, 128/889; 206/440, 441

[56] References Cited

U.S. PATENT DOCUMENTS

| | | |
|---|---|---|
| 3,645,835 | 2/1972 | Hodgson ................................. 161/146 |
| 4,265,234 | 5/1981 | Schaar . |
| 4,334,530 | 6/1982 | Hassell . |
| 4,360,015 | 11/1982 | Mayere . |
| 4,372,303 | 2/1983 | Grossman et al. . |
| 4,374,520 | 2/1983 | Grossman et al. . |
| 4,600,001 | 7/1986 | Gilman . |
| 4,669,458 | 6/1987 | Abraham et al. . |
| 4,753,232 | 6/1988 | Ward . |
| 4,884,563 | 12/1989 | Sessions . |
| 4,948,651 | 8/1990 | DeBusk et al. ........................... 422/110 |
| 5,000,172 | 3/1991 | Ward .......................................... 602/57 |
| 5,106,629 | 4/1992 | Cartmann et al. ....................... 424/445 |
| 5,328,450 | 7/1994 | Smith et al. ............................... 602/59 |
| 5,330,452 | 7/1994 | Zook ....................................... 604/307 |
| 5,501,661 | 3/1996 | Cartmell et al. ........................... 602/58 |
| 5,722,943 | 3/1998 | Sessions . |
| 5,733,251 | 3/1998 | Johns ......................................... 602/57 |
| 5,755,681 | 5/1998 | Plews ........................................ 602/58 |

FOREIGN PATENT DOCUMENTS

| | | |
|---|---|---|
| 0 051 935 | 11/1986 | European Pat. Off. . |
| 0066899 | 3/1988 | European Pat. Off. . |
| 213299 | 6/1984 | United Kingdom . |
| 2157955 | 8/1985 | United Kingdom . |

*Primary Examiner*—Richard J. Apley
*Assistant Examiner*—Kim M. Lee
*Attorney, Agent, or Firm*—Tilton, Fallon, Lungmus & Chestnut

[57] ABSTRACT

A thin film wound dressing is disclosed in which a thin, transparent, vapor-transmitting elastomeric film is coated along its underside with a suitable pressure-sensitive adhesive for securing the dressing to a patient's skin. Prior to use, the adhesive layer is protected by a removable release liner. The opposite (upper) surface of the film has a removable backing layer with a multiplicity of wide openings or foramina separated from each other by connecting strip portions, and at least some of the strip portions preferably terminate in free ends along a peripheral edge of the film.

19 Claims, 1 Drawing Sheet

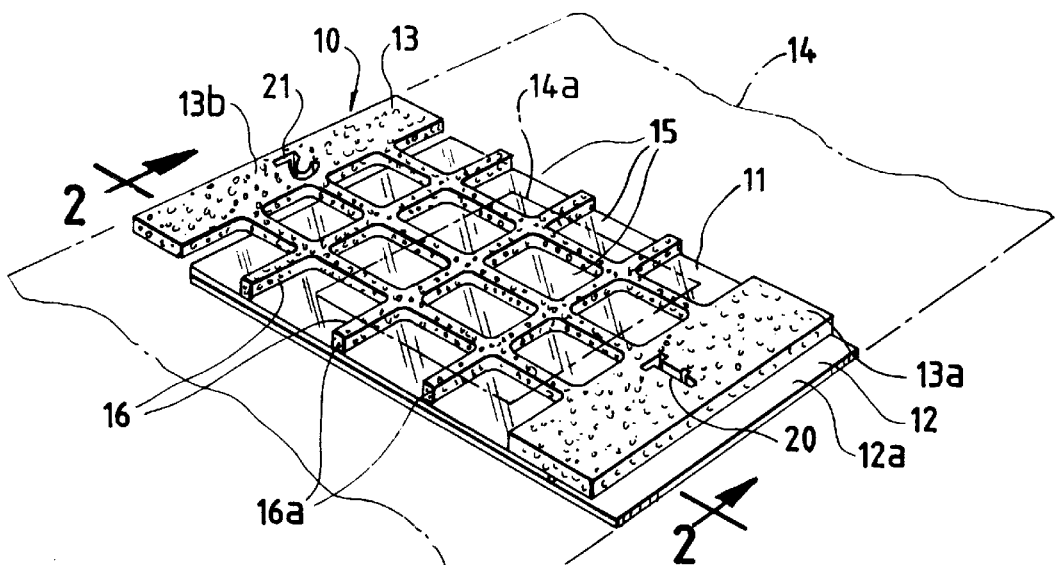
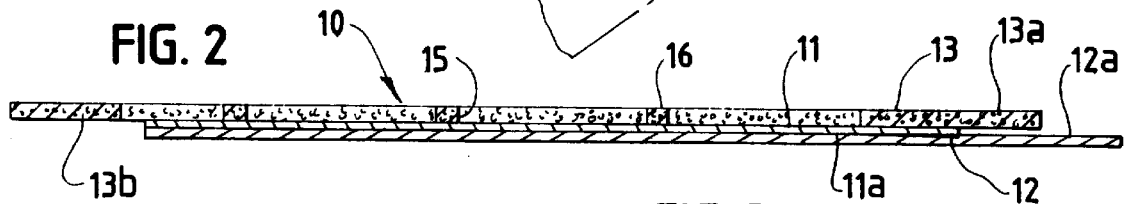
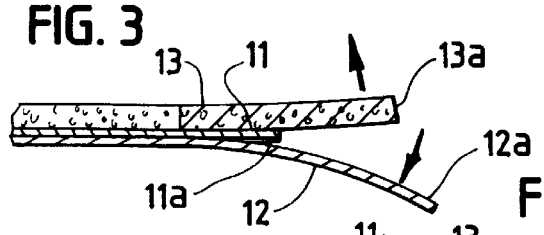
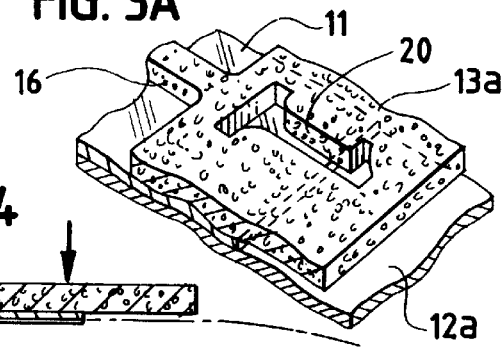
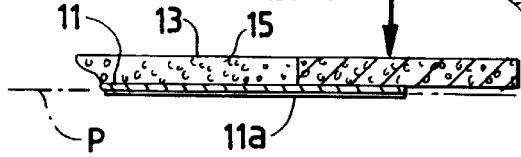
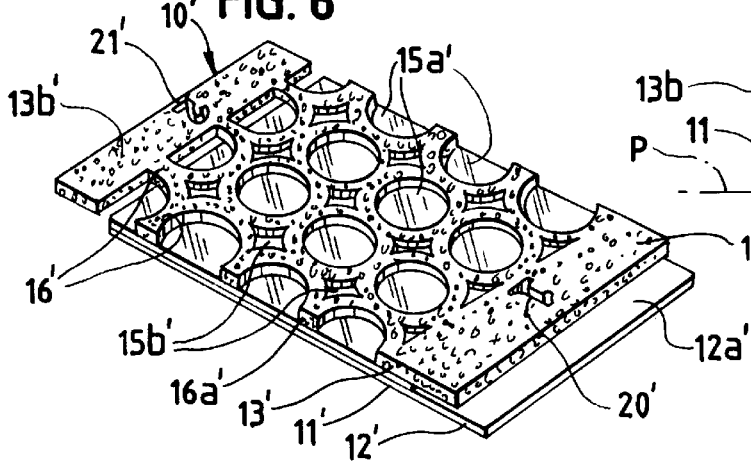
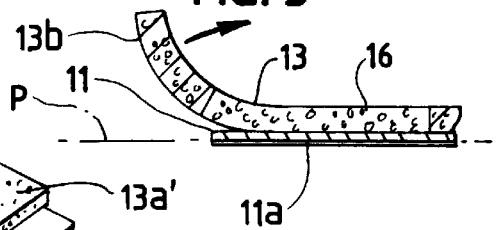

THIN FILM WOUND DRESSING WITH REMOVABLE FORAMINOUS BACKING LAYER

RELATED APPLICATION

This application is a continuation-in-part of our pending application Ser. No. 08/818,504, filed Mar. 14, 1997.

BACKGROUND AND SUMMARY

Thin film wound dressings are widely used in the care of wounds. As disclosed in U.S. Pat. No. 3,645,835, such a dressing consists essentially of a thin film of polyurethane or other suitable elastomer that is capable of transmitting moisture vapor at rates approximating or exceeding those of skin. Such a film is coated along its underside with a pressure-sensitive adhesive that, because of its composition or discontinuity, or both, is also vapor permeable. The result is a dressing that is often referred to as being "breathable," is capable of flexing and stretching and of maintaining a moist environment for a healing wound, and provides a protective bacterial barrier for such a wound.

Because of their flexibility and stretchability, thin film dressings are also useful for other purposes, such as providing protective covers over injection and catherization sites. Such a cover or dressing may readily conform to the contours of a catheter and those of the skin surfaces at an application site, while allowing visual inspection of the site and protecting it against contamination.

Offsetting those advantages is the disadvantage that thin film wound dressings may be difficult to apply, especially for one person. Since such a film is not self-supporting, some means must be provided to prevent it from becoming folded and wrinkled, and adhering to itself, during application. In general, two types of removable "delivery systems" have been developed to support such a dressing as it is delivered from the package to the site of application.

One such support system may be referred to as a removable frame system, and the other as a removable film system. In a removable frame system, a thin film wound dressing is supported by a removable peripheral frame as disclosed, for example, in U.S. Pat. No. 4,372,303 and EP 0 051 935. The frame functions as a device to hold the dressing in generally planar condition until it has made adhesive contact with the attachment site, at which time the frame is ordinarily removed. Such a frame system has the advantage of allowing the transparent film to flex and stretch within the opening of the frame, thus allowing the dressing to conform to the contours of body surfaces, catheters, and the like.

One disadvantage of the frame system is that it is often difficult and time-consuming to remove the frame after the dressing has been applied. Quite commonly such a frame does not peel easily from the film in a single motion but instead must be carefully "teased" away from the edges of the dressing. Another disadvantage of frame systems is that they do not work well should the user wish to cut the dressing to smaller size, since the frame must remain intact for ease of application.

In a film system, the entire upper surface of the dressing has a reinforcing cover that may be peeled away after the dressing is applied. To facilitate application of the dressing, the cover is usually a transparent film, but one that does not have the extensibility and low tensile modulus of the dressing itself. While such a delivery system has the advantage (over a frame system) that the supporting cover may be peeled away easily in one step, it has the disadvantage that the central portion of the dressing is held in relatively stiff condition and cannot readily conform to the irregular or uneven surfaces to which it must be applied. Also, such a support system does not work well if the dressing is to be cut to a smaller size because it may be difficult, sometimes impossible, to start the peel of the cover away from the dressing if the removal tab of the cover is not part of the cut piece.

Accordingly, a main aspect of this invention lies in providing a thin film wound dressing with a flexible support backing that may be easily removed in one peeling motion whether the dressing is to be applied in its original size (as supplied) or as a smaller cut section or piece of the original dressing. The backing effectively supports the wound dressing during application, and, after the dressing has been applied, the backing may be easily gripped and peeled away without at the same time causing the dressing itself to become detached from the skin surfaces to which it has been adhered.

Like prior thin film wound dressings, the dressing of this invention comprises a thin breathable elastomeric film of polyurethane or some other material having similar properties. The underside of the film is coated with a gas-permeable adhesive layer which in turn is covered by a removable release liner of siliconized paper or similar material. The opposite surface of the elastomeric film has a foraminous backing layer of flexible and preferably stretchable material. specifically, the backing layer has a multiplicity of wide openings separated from each other by narrow strip portions of the backing layer. Ideally, at least some of the strip portions terminate in free ends located along a peripheral edge of the elastomeric film.

The flexible backing layer is removably attached to the upper surface of the elastomeric film. A releasable attachment may take the form of a pressure-sensitive adhesive or a thermal bond. In either case, the strength of the bond between the flexible backing and the film should be greater than the strength of an equal area of the adhesive bond between the film and the removable release sheet or liner. Most advantageously, the liner protrudes beyond an edge of the film and an imperforate portion of the backing directly thereabove, with the result that the release liner may be easily peeled away from-the film without disrupting the bond between the film and its flexible backing. However, once the dressing is in place, the flexible backing may itself be peeled away from the film, without disrupting the adhesive attachment between the film and the patient's skin, because most of the backing is secured to the film only along the narrow strip portions of the backing. If at least some of the strip portions have free ends terminating along the edge of the film, a user may simply grip one of those free ends to initiate the peeling action for removing the backing from the applied thin film dressing. Alternatively, a user may grip one of the strip portions between the multiplicity of window openings in the foraminous backing and pull the strip portion upwardly to commence peeling of the backing from the applied thin film dressing.

In a preferred embodiment, the flexible foraminous support backing has a generally imperforate first tab portion that extends beyond the film along at least a portion of its periphery, and the release liner projects outwardly beyond that tab portion and well beyond the peripheral edge of the film. The backing layer may include a generally imperforate second tab portion that is connected to a plurality of the strip portions and is located outwardly beyond an edge of the film opposite from the first tab portion. The release liner may be easily peeled away from the rest of the dressing by commencing the peeling action in the area of the first tab portion and then, after the dressing has been applied, the removable backing layer may be peeled away from the applied film by drawing back on the second tab portion.

To assist a user in ascertaining the tab portions for the proper sequence of the first and second peeling steps, such tab portions are preferably provided with suitable alphanumeric indicia. A particularly effective way of doing so takes the form of providing the respective tab portions of the removable support backing with distinctive alphanumeric cutouts indicating the proper sequence for the successive peeling steps.

The openings in the backing layer may be regular or irregular in shape and should be of an average size within the range of about 0.5 cm$^2$ to about 9 cm$^2$, with a preferred area averaging about 1 cm$^2$ to about 4 cm$^2$. In one embodiment, such openings have the shape of an equilateral rectangle (i.e., are generally square) but in other embodiments such openings may be of the shape of other substantially regular polygons (i.e., hexagon, octagon, etc.) or may be rounded (e.g., oval or circular) or a combination of rounded and non-rounded. It is important that such openings, or at least a large proportion of them, be wide in contrast to elongate; that is, two cross dimensions of such an opening measured at right angles should be approximately the same so that the strip portions between those openings will provide adequate support for the thin film of the dressing and still define openings large enough, and regular enough, that a user may insert his/her fingers into the openings to grasp a strip portion of the backing in order to peel that backing away from the film.

The removable and formaminous support backing must be flexible and, in a preferred embodiment, takes the form of a soft, flexible polymeric foam. While the backing layer may or may not be stretchable, stretchability is considered highly desirable. Where a stretchable backing layer is used, the extensibility of the backing layer without breaking should be to at least 120% of its original length, preferably to at least 150% of its original length. Also, its modulus should be low enough so that the support backing does not objectionably reduce the stretchability and conformability of the film when the dressing is being applied. To that end, the material of the support backing should be capable of extending to 110% of its original length with a force of less than about 1000 pounds per square inch, preferably less than about 500 pounds per square inch, when tested at an extension rate of 10 times the sample length per minute.

The strip portions between the openings of the support backing should have a width generally falling within the range of about 1 mm to about 4 mm, and the thickness of the backing layer should be in the range of about 0.2 mm to about 2.0 mm (preferably 0.5 mm to 1.0 mm). By virtue of its thickness, the support backing greatly increases the bending modulus of the dressing, thereby making it self-supporting.

Other advantages, objects, and features of the invention will become apparent from the specification and drawings.

DRAWINGS

FIG. 1 is a perspective view of a wound dressing embodying the invention.

FIG. 2 is an enlarged sectional view taken along line 2—2 of FIG. 1.

FIG. 3 is an enlarged fragmentary sectional view illustrating a first step in the use of the dressing, namely, the removal of the release liner.

FIG. 3A is an enlarged fragmentary perspective view illustrating details of the alphanumeric cutout of a tab portion of the dressing.

FIG. 4 is a fragmentary sectional view depicting the step of applying the dressing to a receiving surface.

FIG. 5 is a sectional view illustrating the final step of peeling the foam backing away from the adhesively-applied film.

FIG. 6 is a perspective view depicting second embodiment of the invention.

DETAILED DESCRIPTION OF PREFERRED EMBODIMENTS

Referring to the drawings, numeral 10 generally designates a wound dressing comprising a thin, transparent, elastomeric film 11, a release liner 12, and a foraminous and stretchable backing layer 13. In the embodiment illustrated, the dressing is generally rectangular in outline and may be a cut section of a larger dressing indicated by phantom lines 14. If desired, the larger dressing may be supplied in roll form and each smaller dressing 10 may be cut from the roll to the size and shape desired by the user. A particular advantage of dressings made in accordance with this invention is that their size may be varied by the user without creating later problems in separating the layers from each other. Thus, if the dressing were of an even smaller size and shape indicated by phantom lines 14a, the backing of that dressing could still be easily peeled away from film 11.

The transparent elastomeric film 11 may be formed of polyurethane or any other moisture-vapor permeable film having similar properties as well known in the art. Elastomeric polyester or polyether block amide films may also be used. U.S. Pat. No. 3,645,835 describes such films and methods of making such films and testing their permeability. For use as a thin film wound dressing, the film 11, including the adhesive coating 11a along its underside, should transmit moisture vapor at a rate equal to or greater than that of human skin.

The pressure-sensitive adhesive used for coating 11a may be any suitable medical-grade adhesive commonly used for thin film wound dressings. Acrylate polymers or copolymers of the type described in U.S. Pat. No. 5,531,855 are believed particularly suitable. As noted above, the adhesive coating 11a should be capable of transmitting moisture vapor at a rate greater to or equal to that of human skin. While such a characteristic may be achieved through the selection of the adhesive composition, other methods of achieving a relatively high moisture-vapor transmission rate may be used, such as pattern coating the adhesive on the underside of film 11.

Release liner 12 may be formed of silicone-coated paper or any other suitable material such as polyethylene, polypropylene or polyester coated with silicone or other release agent. Such a release liner should be flexible but substantially non-stretchable so as to provide support for the elastomeric dressing 11 (including adhesive 11a) carried by it. As shown most clearly in FIGS. 1 and 2, an edge portion 12a of the release liner extends outwardly beyond an edge of film 11 and backing 13 to provide a gripping portion that facilitates removal of the release liner when the dressing is to be applied to a receiving surface.

The flexible and removable backing layer 13 has a multiplicity of openings 15 separated by strip portions 16 which, in the embodiment depicted in FIGS. 1–5, are rectilinear and arranged in the form of a grid. Each opening 15 is generally square and has an area within the general range of about 0.5 cm² to about 9 cm². In FIG. 1, the openings are generally of uniform size but some variations are permissible as long as the average size falls within the general range stated above. A preferred average size range is believed to be about 1 cm² to about 4 cm.

The strip portions 16 that define the openings 15 are relatively thin or narrow, each having a width within the range of about 1 mm to about 4 mm. The narrowness of the strip portions is particularly important in providing a grid that does not obstruct a clear view of the wound site during and following application of the dressing. Since the grid is secured to the top surface of the film and is of substantial thickness, it significantly increases the bending modulus of the dressing, thus making it self-supporting.

Soft flexible polymeric foam materials are believed particularly suitable for use as the formaminous support backing, but other materials having similar properties, such as soft foam-like fabric, may also be used. The foam or fabric should be highly flexible but may or may not be stretchable. For example, a soft, polymeric foam layer having extensible properties may be laminated to a thin film which prevents or greatly reduces such extensibility, the two layers of the laminate together constituting the flexible foraminous backing layer. Important advantages are achieved with respect to removability even where the foraminous backing is non-stretchable or has only limited stretchability but, in a preferred embodiment of the invention, the backing layer 13 is both flexible and stretchable and, therefore, does not restrain stretching of the elastomeric film 11 as it conforms to uneven or irregular surfaces during application of the dressing. The backing layer 13 may be contractable as well as extensible, but contractability may not be advantageous, particularly in a dressing as disclosed in which the support backing is to be removed after the dressing is applied.

If the support backing is to be sufficiently extensible to permit stretching of the elastomeric film 11 as that film is applied to uneven or irregular surfaces in use of the dressing, the backing should be able to extend without breaking to at least 120%, and preferably to at least 150%, of its original length (or width). The force required for such extension should also be relatively low. More specifically, the force required to stretch such material 110% of its original dimensions should be less than about 1000 pounds per square inch, and preferably less than 500 pounds per square inch, when tested at an extension rate of 10 times the sample length per minute.

Closed cell olefin foams, such as polyethylene vinyl acetate copolymer foams available under the designations Volara EO #6 and EO #12 from Voltek of Lawrence, Mass. are considered particularly effective for the removable and foraminous backing layer 13, but other closed cell foams are also believed suitable. Any of a number of open-cell foams having similar properties, such as polyurethane foams, may be used. With respect to fabrics having foam-like properties, spunbonded fabrics of bicomponent thermoplastic fibers that are through-air heat bonded, such as those available from Kimberly-Clark Corporation, Neenah, Wis., are believed suitable. Other synthetic fabrics of through-air bonded or infrared-bonded bicomponent fiber carded webs may also be used. Particularly effective results have been obtained with a backing layer having a thickness within the range of about 0.2 mm to about 2.0 mm, the preferred range being about 0.5 mm to about 1.0 mm.

The attachment between backing layer 13 and film 12 may be provided by a suitable pressure-sensitive adhesive or, if desired, the attachment may be in the form of a thermal bond. In either case, the attachment is releasable, allowing the backing layer to be peeled away from the upper surface of the film after the dressing has been applied to a receiving surface. A pressure-sensitive adhesive similar to the one used to attach release liner 12 to the underside of film 11 may be used and, if desired, the upper surface of the film may be provided with a release coating of silicone or other suitable release agent to facilitate ease of separation when the backing is to be peeled away from the film. Preferably, the adhesive (or the thermal bond) between the backing layer and the film is stronger per unit area than the strength of the attachment between the film and the release liner to eliminate or reduce the possibility that the support backing and film will become separated when the release liner is peeled away.

In a preferred embodiment, strip portions 16 terminate in free ends 16a along one or more edges of film 11, two such edges on opposite sides of the dressing being shown in FIG. 1. As a result of such construction, a user may easily separate the foam backing layer from the film by simply gripping one of the free end portions and pulling it back from the film to commence the peeling operation. Such a peeling step would be undertaken after film 11 has been adhesively applied to the patient's skin (or other receiving surface) and, because the peeling force is localized along the undersides of the narrow strip portions 16, there is little if any possibility that such peeling action would cause the film to lift away from the surface to which it is adhered.

In the embodiment of FIGS. 1–5, the grid-like backing layer has an imperforate tab portion 13a extending along one side edge of the dressing. Extension 12a of release liner 12 is located along the same side edge. The purpose of imperforate tab portion 13a is to provide a greater area of sealing contact between the backing layer 13 and the film 11 adjacent extension 12a of the release liner so that when the release liner is peeled downwardly as shown in FIG. 3, the film 11 will remain with the backing layer 13 and will separate cleanly from the liner.

As shown in the drawings, the tab portion 13a also projects well beyond the edge of the elastomeric film 11. The advantage of such a construction is that after the release liner 12 is peeled away (FIG. 3), a user may hold the dressing by the tab portion 13a, without making finger contact with adhesive layer 11a. Finger contact with an adhesive-coated surface (especially if the user is wearing surgical gloves, as would normally be the case in handling a wound dressing) could present difficulties that are avoided by the construction shown.

A second tab portion 13b extends along the opposite side edge of the dressing and is disposed outwardly beyond the adjacent edge of film 11. Like the first tab portion 13a, portion 13b is imperforate—that is, it is free of openings 15. The second tab portion is integrally connected to a plurality of strip portions 16 that extend to, and preferably project slightly beyond, the adjacent edge of film 11. Therefore, after the dressing has been adhesively applied to the patient's skin P, the backing layer may be peeled away by simply drawing back the second tab portion 13b in the manner depicted in FIG. 5.

FIGS. 3–5 therefore illustrate three steps in the application of dressing 10. The release liner 12 is first peeled away (FIG. 3) and the dressing is then adhesively secured to the patient (FIG. 4). During the securing step, proper orientation of the dressing is readily achieved because of the transparency of film 11 and the multiplicity of openings or apertures 15 in backing layer 13. Thereafter, the support backing is peeled away, leaving the thin film wound dressing adhesively secured to the patient (FIG. 5).

To help insure that a user will commence the step of peeling away the release liner 12 from the edge of the dressing along tab portion 13a, that portion may be provided with a suitable indicium or indicator 20 such as the numeral "1" or the letter "A." Tab portion 13b along the opposite edge of the dressing would then be provided with a further indicium or indicator 21 such as the numeral "2" or the letter "B." Most advantageously, both indicia take the form of cutouts extending completely through the thickness of the respective tab portions as indicated clearly in FIG. 3A.

The dressing 10' of FIG. 6 differs from the dressing just described only with respect to the shape and arrangement of the multiplicity of openings 15a' and 15b' in backing layer 13' and the strip portions 16' between those openings. Unlike rectangular openings 15, openings 15a' are circular in shape and the strip portions 16' are arcuate or curvilinear. Such strip portions also define smaller openings 15b' of non-circular shape. Although the openings 15a' and 15b'. are of different sizes and shapes, their average size falls within the same ranges previously specified. As in the first embodiment, strip portions 16' terminate in free ends 16a' along one or more edges of the dressing. The backing layer 13' is also provided with first and second tab portions 13a' and 13b' which function in the same manner as tab portions 13 and 13b of the first embodiment.

While in the foregoing, we have disclosed embodiments of the invention in considerable detail for purposes of illustration, it will be understood by those skilled in the art that many of these details may be varied without departing from the spirit and scope of the invention.

What is claimed is:

1. A wound dressing comprising a thin, transparent, vapor-transmitting elastomeric film having upper and lower surfaces; a layer of pressure-sensitive adhesive along said lower surface and a protective release liner removably covering said adhesive layer; and a foraminous backing layer of flexible material removably secured to said upper surface; said backing layer having a multiplicity of openings separated from each other by integral strip portions of said backing layer.

2. The dressing of claim 1 in which said removable backing layer has said strip portions thereof adhesively secured to said film.

3. The dressing of claim 1 in which said removable backing layer has said strip portions thereof thermally sealed to said film.

4. The dressing of claim 1 in which said openings are rectangular and said strip portions are rectilinear and define a grid pattern.

5. The dressing of claim 1 in which said openings are non-rectangular and said strip portions are curvilinear.

6. The dressing of claim 1 in which said openings of said removable backing layer are of an average size falling within the range of about 0.5 cm$^2$ to about 9 cm$^2$.

7. The dressing of claim 6 in which said average size of said openings falls within the range of about 1 cm$^2$ to about 4 cm$^2$.

8. The dressing of claim 6 in which said strip portions are of a width falling within the range of about 1 mm to about 4 mm.

9. The dressing of claim 1 in which said removable backing layer comprises a layer of soft, flexible polymeric foam.

10. The dressing of claim 9 in which said removable backing layer has a thickness within the range of about 0.2 mm to about 2.0 mm.

11. The dressing of claim 10 in which said thickness of said backing layer is within the range of about 0.5 mm to about 1.0 mm.

12. The dressing of claim 10 in which said removable backing layer is formed of a polymeric foam that is stretchable and has extensibility without breaking of at least 120% of its original length and has a stress at 110% of its original length of less than about 1000 pounds per square inch.

13. The dressing of claim 1 in which said removable backing layer includes a generally imperforate first tab portion overlying said film along at least a portion of said peripheral edge thereof; said release liner projecting outwardly beyond said film along a portion of said peripheral edge.

14. The dressing of claim 13 in which said first tab portion extends beyond said film along a portion of said peripheral edge thereof.

15. The dressing of claim 14 in which said release liner projects outwardly beyond said first tab portion along said peripheral edge of said film.

16. The dressing of claim 14 in which said backing layer includes a generally imperforate second tab portion connected to a plurality of said strip portions and disposed outwardly beyond said film.

17. The dressing of claim 16 in which said first tab portion is provided with indicia means for indicating the edge of the dressing from which a step of peeling said release liner from said layer of pressure-sensitive adhesive should be commenced.

18. The dressing of claim 17 in which said second tab portion is provided with indicia means sequentially following the indicia means of said first tab portion for indicating the edge of the dressing from which a step of peeling said backing layer from said elastomeric film should commence.

19. The dressing of claim 18 in which said indicia means of said first and second tab portions comprise cutouts extending through the thickness of said backing layer of said first and second tab portions, respectively.

* * * * *